[19] United States Patent
Pawliszyn

[11] Patent Number: 5,496,741
[45] Date of Patent: Mar. 5, 1996

[54] DEVICE AND PROCESS FOR INCREASING ANALYTE CONCENTRATION IN A SORBENT

[75] Inventor: Janusz B. Pawliszyn, Waterloo, Canada

[73] Assignee: University of Waterloo, Waterloo, Canada

[21] Appl. No.: 227,321

[22] Filed: Apr. 14, 1994

[51] Int. Cl.[6] .......................... G01N 21/03; G01N 21/77
[52] U.S. Cl. .......................... 436/163; 436/169; 436/171; 436/178; 422/58; 422/59; 422/82.06; 422/82.09; 422/102; 95/285
[58] Field of Search .................................. 436/165, 169, 436/171, 178; 422/58, 59, 69, 82.06, 82.09, 90, 102; 95/285; 73/863.72; 137/625

[56] References Cited

U.S. PATENT DOCUMENTS

| D. 319,879 | 9/1991 | Wachob et al. | D24/108 |
|---|---|---|---|
| 4,081,402 | 3/1978 | Levy et al. | 252/428 |
| 4,147,764 | 4/1979 | Levy et al. | 424/1 |
| 4,362,356 | 12/1982 | Williams et al. | 350/96.20 |
| 4,388,272 | 6/1983 | Gesteland | 422/102 |
| 4,966,695 | 10/1990 | Joshua | 210/198.2 |
| 5,105,851 | 4/1992 | Fogelman | 137/625.11 |
| 5,142,143 | 8/1992 | Fite et al. | 250/288 |
| 5,153,666 | 10/1992 | Pawliszyn | 356/128 |
| 5,169,521 | 12/1992 | Oka et al. | 210/198.2 |
| 5,237,824 | 8/1993 | Pawliszyn | 62/51.1 |
| 5,250,093 | 10/1993 | Jiang et al. | 96/102 |
| 5,279,742 | 1/1994 | Markell et al. | 210/638 |
| 5,302,191 | 4/1994 | Koutrakis et al. | 95/285 |
| 5,304,493 | 4/1994 | Nowak | 436/56 |
| 5,358,557 | 10/1994 | Jiang et al. | 95/82 |

FOREIGN PATENT DOCUMENTS 9115745  10/1991  WIPO.

OTHER PUBLICATIONS

"New Solvent–free Samples Preparation Techniques", Environ Sci. Technol vol. 28 No. 13 1994.

Primary Examiner—Timothy M. McMahon
Assistant Examiner—N. Bhat
Attorney, Agent, or Firm—Daryl W. Schnurr

[57] ABSTRACT

A device and process for increasing analyte concentration in a sorbent from a source of analytes contained in a sample uses means for increasing a temperature differential between the sample and the sorbent. The sorbent can be a polymeric coating on a substrate. The sorbent is located in a headspace of the sample and has internal cooling means such as liquid carbon dioxide so that the sorbent can be cooled relative to the sample. Preferably, the sample is heated to further increase the temperature differential between the sample and the sorbent. As the temperature differential increases, a partition coefficient of the sorbent/sample also increases. Preferably, the sorbent is located in a headspace of the sample. Previously, for certain analytes, the partition coefficient was too low and the concentration of analytes extracted into the sorbent from the sample was insufficient to provide an accurate measurement of concentration.

33 Claims, 3 Drawing Sheets

5,496,741

DEVICE AND PROCESS FOR INCREASING ANALYTE CONCENTRATION IN A SORBENT

BACKGROUND OF THE INVENTION

1. Field of the Invention

This invention relates to a device and process for increasing analyte concentration in a sorbent from a source of analytes contained in a sample by increasing a temperature differential between said sample and said sorbent.

2. Description of the Prior Art

As described in International Application Number PCT/CA91/00108 filed on Apr. 2nd, 1991 by Janusz B. Pawliszyn entitled Method and Device for Solid Phase Microextraction and Desorption, it is known to extract analytes using a fiber (either uncoated or coated with a polymeric coating) to extract organic compounds from their matrix and to directly transfer the analytes to an analytical instrument through thermal desorption. For example, the analytes can be transferred into a gas chromatograph through thermal desorption in a GC injector. The fiber can extract the analytes by dipping all or part of the fiber directly into the sample containing analytes or by contacting the fiber with a headspace located above the liquid containing analytes. This process is referred to as solid phase microextraction (hereinafter "SPME"). SPME has been used successfully for analyzing volatile organic compounds (those listed in U.S. Environmental Protection Agency Method 624, polyaromatic hydrocarbons (PAH's), polychlorinated biphenyls, phenol and its derivatives in aqueous samples. SPME can also be used to analyze volatile and semi-volatile organic compounds in more complex samples such as soil and sludge by having the analytes contact the fiber in a headspace above the sample matrix. Sometimes, the SPME approach suffers from disadvantages in that many matrices do not release sufficient analytes. Thus, the analytes transferred to the fiber are not sufficient to produce a detectable signal when the analytes are desorbed in an analytical instrument. Also, the SPME is typically not a quantitative extraction method and therefore, it requires careful calibration procedures.

SUMMARY OF THE INVENTION

It is the object of the present invention to provide a device and process whereby analyte concentration in a polymer from a source of analytes contained in a sample is increased.

A device for increasing analyte concentration in a sorbent using a source of analytes contained in a sample has a sorbent and a source of analytes contained in a sample. The sorbent is located to contact said sample, with cooling means to cool said sorbent, thereby increasing temperature differential between said sample and said sorbent.

A process for increasing analyte concentration in a sorbent from a source of analytes contained in a sample, with means to cool said sorbent, said process comprising locating said sorbent so that it can be contacted by said analytes and activating the means to cool the temperature differential between said sample and said sorbent.

DESCRIPTION OF A PREFERRED EMBODIMENT

Figure 1:
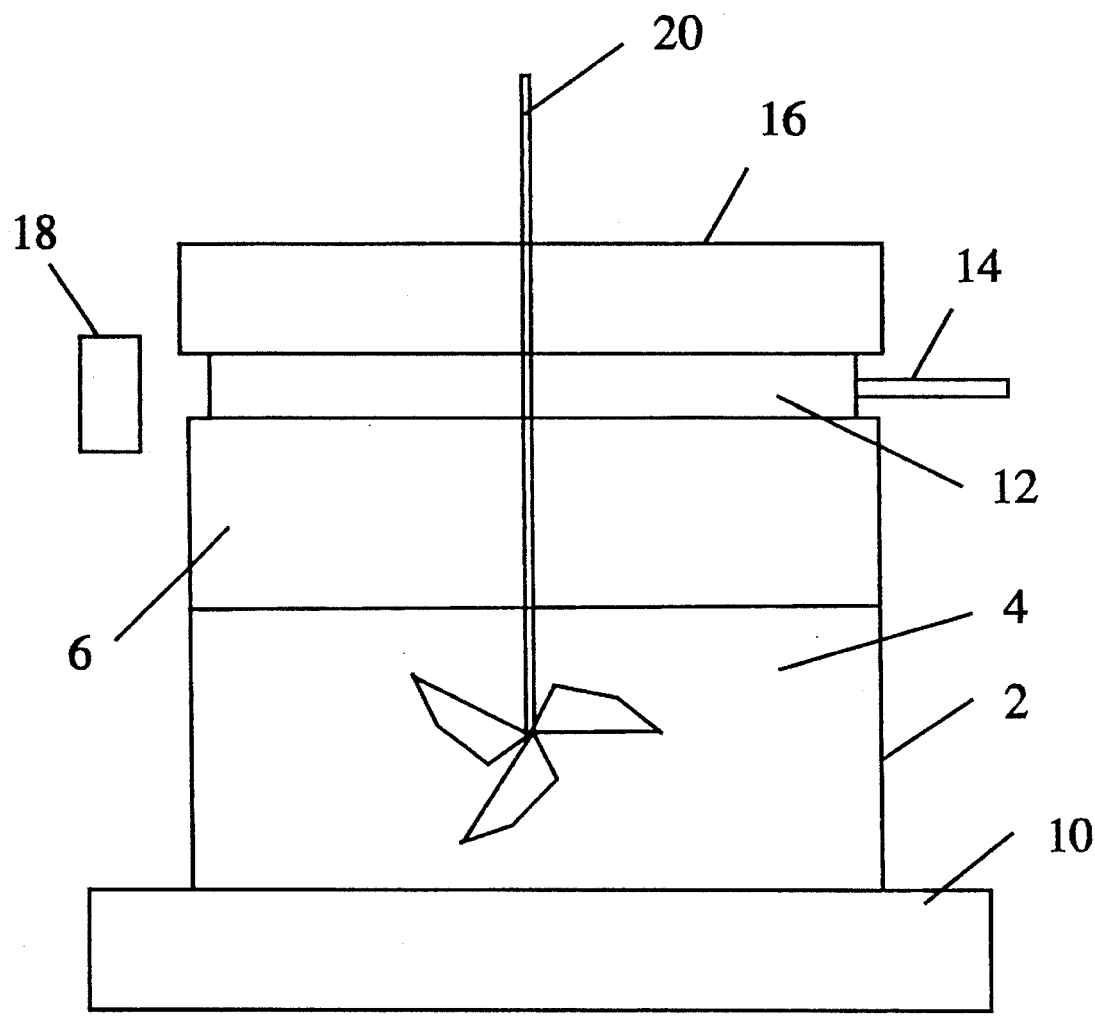
FIG. 1 is a sectional side view of a sample container having a headspace.

In FIG. 1, a container 2 contains a sample 4. The sample has a headspace 6 located above the sample. A polymer 8 is a sorbent. The sample contains analytes (not shown) and a polymer 8 is located in said headspace. The polymer 8 is removable from the container 2. A hotplate 10 is means for heating the sample 4. The connections for the hotplate 10 are conventional and are not shown. The polymer 8 has a coating 12 thereon and has optical fibers 14 extending therethrough. A Peltier cooling device 16 is connected to cool the polymer. The optical fibers 14 are used to pass electromagnetic waves through the sorbent. A detector 18 measures the absorbence of said waves compared with the absorbence when no analytes are present to determine the concentration of said analytes in said sorbent. Preferably the electromagnetic waves are light waves. An agitator 20 is suitably connected to rotate about its longitudinal axis to stir the sample. The agitator is conventional and the power source and the manner in which it is connected are not shown.

Figure 2:
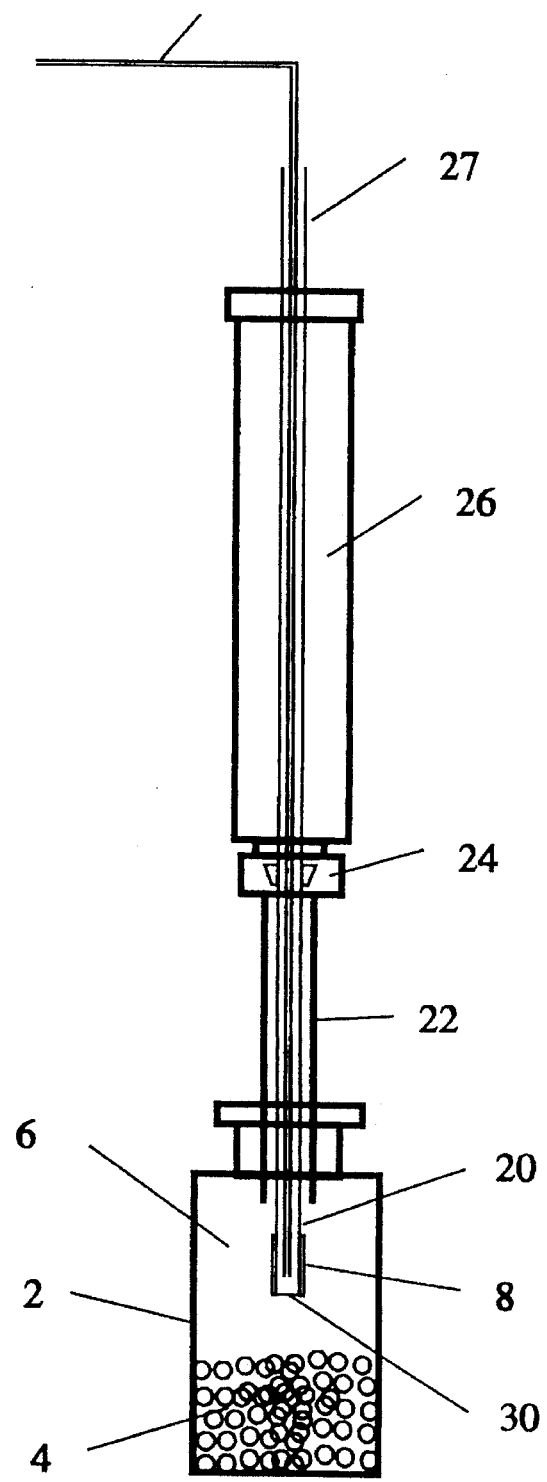
FIG. 2 is a schematic side view of a syringe mounted to hold a sorbent in a headspace of a container where said sorbent is cooled internally by liquid carbon dioxide.

In FIG. 2, the container 2 contains the sample 4 and the headspace 6. A polymer coating 8 is located on a substrate 20. The substrate 20 is preferably a hollow fiber. The fiber is surrounded by a housing 22 and is connected through a ferrule 24 to a barrel 26. The fiber 20 can be moved longitudinally relative to the housing 22 by using a plunger 27, being an outer end of the filter 20. The barrel 26, housing 22 and plunger 27 constitute a syringe. Within the hollow fiber 20, there extends a capillary 28 that is sized to fit easily within said fiber. An inner end of the capillary is located adjacent to the polymer 8. An outer end of the capillary is connected to cooling means (not shown) for said polymer. Preferably, the cooling means is a source of liquid carbon dioxide which preferably is contained in a gas cylinder under pressure. An end 30 of the fiber 20 is sealed off so that the carbon dioxide gas enters through the inner capillary 28 and escapes in an annular space between the capillary 28 and the hollow fiber 20.

As an example, the SPME device shown in FIG. 2 can have a silica fiber 20 with 673 µm O.D. and 537 µm I.D. The fiber can be sealed at the end 30 by heating that end to about 800° C. A poly(dimethylsiloxane) liquid polymer tubing with a thickness of 340 µm and a length of one centimeter was swollen in hexane and then placed on an outer surface of the fiber 20 to form a concentric sheath at the sealed end 30 representing the coating 8. An outer end of the fiber 20 opposite to the end 30 is used as the plunger to move the coating longitudinally relative to the housing. The inner silica capillary 28 has a 375 µm O.D. and a 50 µm I.D. The inner capillary delivers liquid carbon dioxide from a $CO_2$ cylinder. The small inside diameter of the inner capillary also serves as a restrictor to the limit the flow of $CO_2$. Thus, the temperature of the coating 8 can be controlled by using an inner capillary with different inside diameters to control the flow rate of liquid $CO_2$. An inner capillary with an inside diameter of 50 µm was proven to give the best flow rate of liquid $CO_2$, the flow rate being fast enough to cool the coating sufficiently while not being so fast as to freeze the syringe. The syringe barrel was a Hamilton 1710RM gas tight syringe barrel. The plunger and needle of the syringe was discarded and the needle was replaced with a 17 gauge housing. The ferrule in the 1710RM syringe was modified by enlarging the center hole to accommodate the large housing size. The temperatures in the matrix, headspace and fiber coating surface during the internally cooled fiber extraction were measured by using a thermocouple. The gas chromatograph-mass spectrometer used here was a VARIAN SATURN I (a trade mark) coupled with a VARIAN 3400 GC (a trade mark). A 30 meter VOCOL (a trade mark) column with 1.5 μm stationary phase, 0.25 mm I.D. and 0.4 mm O.D. was used in the VARIAN 3400 GC. The gas chromatograph was also equipped with a septum-equipped temperature programmable injector. All chemicals were of ACS grade and deionized water was used for sample preparation.

Figure 3:
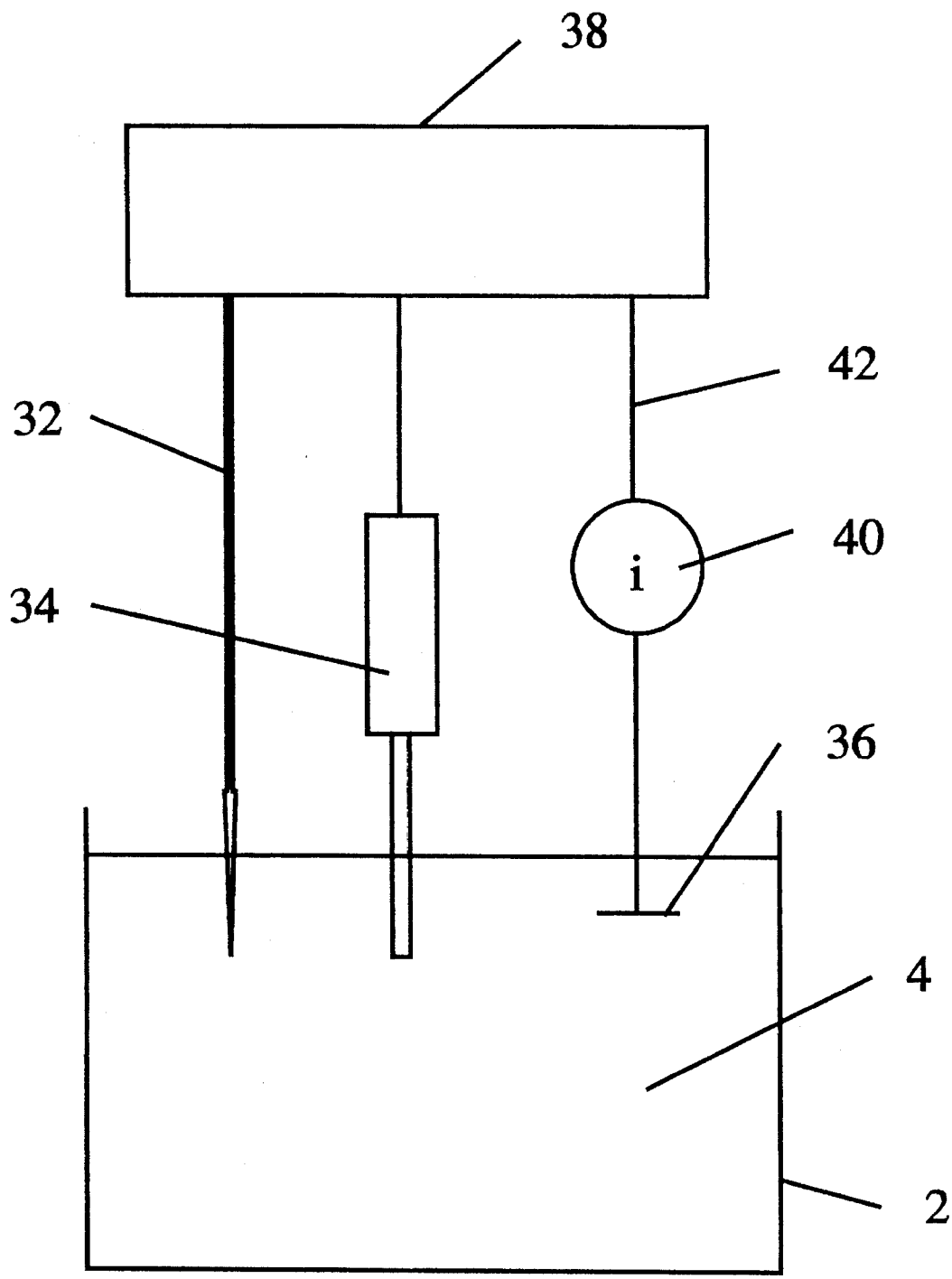
FIG. 3 is a sectional side view of an electrochemical cell where one of the electrodes is a sorbent.

In FIG. 3, the container 2 contains the sample 4 with a reference electrode 32, a working electrode 34 and a counter electrode 36 all extending between a potentiostat 38 into the sample 4. For ease of illustration, the cooling means for the sorbent has been omitted from the drawing. An ammeter 40 is connected in a line 42 extending between the counter electrode 36 and the potentiostat 38. The reference electrode 32 is silver-coated with silver oxide. The working electrode 34 is a gold-coated platinum wire and the counter electrode 36 is a platinum wire. The sample 4 contains mercury ions in the form $Hg^{2+}$ and $(Hg)^{2+}$ and free mercury is absorbed by the gold coating on the electrode 34. Conducting polymers, for example, poly(2-vinylpyridine) are used as the electrode coating for the working electrode 34 to reduce acids and aldehydes to less polar analogs which will be much easier to partition onto the organic coating. As another example, a carbon electrode coated with mercury can be used to deposit various metal ions. The electrodes add electrons to the ions in a redox reaction. The working electrode 34 in practice would be the syringe of FIG. 2 with the fiber 20 and coating 8 being the gold-plated platinum wire.

Another approach of increasing concentration of analytes from a sample into a polymer is to add reagents to the sample to convert the analytes into compounds which have a higher affinity towards the polymer and better chromatographic properties. For example, phenols can be converted to acetylated derivatives. For example, reagents can be added to a sample containing phenols to increase the affinity of the phenols for a polymer coating, for example, poly(dimethylsiloxane). Derivatization of the phenols can be carried out with acetic anhydride to form phenol acetates. The phenol acetates are less polar as the hydroxl group is replaced with an acetate group. The acetates have more affinity toward the polymer coating. Certain nitrophenols did not undergo the derivatization reaction with acetic anhydride. Derivatization is carried out to increase affinity and to better enhance detection. Salt can be added to the sample to enhance extraction. Further, where the sorbent is a polymer, diazo reagents can be added to said polymer to convert carboxylic acids and chlorinated carboxylic acids to esters. The diazo reagents are selected from the group consisting of 1-pyrenyldiazomethane and trimethylsilyl-diazomethane. Still further, acids and aldehydes can be reduced to less polar analogs.

Various coatings are suitable including polysiloxane, poly(acrylate), carbowax, gold and an ion exchanger. When poly(acrylate) is used as the coating for phenol analysis, it was found that all of the target compounds were extracted but forty minutes was required for all units to reach equilibrium. Poly(acrylate) is a semi-solid above its glass temperature and below its melting point. The slower equilibration time compared to poly(dimethylsiloxane) is due to the fact that poly(dimethylsiloxane) is a polymeric liquid whereas poly(acrylate) coating is a solid.

By sampling organic analytes from a headspace above a sample matrix, SPME can be used to analyze volatile and semi-volatile organic compounds in more complex samples such as soil and sludge. Since the fiber is not in direct contact with the matrix, target analytes from virtually any matrix can be analyzed. One of the difficulties, particularly for some soil matrices, is that due to possible chemisorption of the analytes in the solid matrices, very few analytes are released through the headspace under normal conditions. One method of causing increasing analytes to be released is to use thermal desorption. Heating the sample to an elevated temperature provides energy for analyte molecules to overcome the energy barrier which ties them to the matrix, thereby enhancing the mass transfer process and increasing the volatility of the analytes. The absorption of analytes by a polymeric coating is an exothermic process, which means that high temperature can adversely affect the absorption of analytes by the coating. As heating increases the temperature of the sample, the coating/headspace partition coefficients of analytes decrease. Since heating also increases the concentration of analytes in the headspace, initially the heating may improve the sensitivity of headspace SPME sampling as well as the speed of extraction. As temperature increases further, the decrease of the partition coefficient can no longer be offset by the increase of concentration in the headspace and the sensitivity drops. As a result, there is usually an optimum temperature for headspace SPME sampling. By maintaining the coating at low temperature and creating a temperature gap between the coating and the headspace, the coating/headspace partition coefficient for the analytes can be dramatically increased resulting in very high sensitivity.

For extraction using the internally cooled SPME device shown in FIG. 2, the sample (water or soil) is first heated in a capped vial by a heat jacket. Next, the fiber is introduced into the headspace above the sample in the vial. A liquid carbon dioxide cylinder is opened to deliver the $CO_2$ coolant to the fiber. During extraction, the heat jacket heats the vial while the liquid carbon dioxide cools the fiber and the fiber coating. It was found that a maximum amount of analytes can be extracted if the headspace temperature is at 110° C. for sand samples and at 80° C. for aqueous samples. After a predetermined sampling time is reached, the supply of liquid $CO_2$ is shut off and the fiber is immediately transferred into a GC injector for thermal desorption and analysis.

In another example, an aqueous BTEX (benzene, toluene, ethylbenzene and xylene isomers) standard solution with a concentration of about 100 ppm was prepared by directly spiking 1 μL pure BTEX compounds into 10 mL deionized water. The exact concentration of this standard solution was determined by injecting 0.2 μL this BTEX/water mixture into a GC/MS for separation and quantitation. The water and soil samples used for the experiments were prepared by spiking 0.2 μL of the BTEX/water standard solution into the sample matrices. Standard solutions of BTEX in methanol were also prepared by spiking pure BTEX compounds into methanol. Some aqueous and soil samples were prepared by spiking BTEX/methanol standards. Various analytes can be used in addition to BTEX including polyaromatic hydrocarbons, pesticides, aliphatics, phenols, ketones, acids, alcohols and organochlorine compounds.

Two kinds of vials were used: 3.7 mL vials were used for the analysis of soil samples with 2 grams of sample in the vial; 1.8 mL vials were used for the analysis of water samples.

The GC method for analyzing BTEX is as follows: the column was maintained at 50° C. for 1 minute; ramp to 80° C. at 20° C./minute, and then ramp to 150° C. at 60° C./minute. The transfer line to the mass spectrometer was maintained at 220° C. during the analysis.

For fiber injection, the injector was maintained at 150° C. during the GC run, while for syringe injection, the injector was at 50° C. and rapidly ramp to 220° C. at the rate of 250° C./minute, and maintained at 220° C. for the rest of GC run. The MS signal was calibrated by injecting BTEX/methanol standards.

During SPME, the amount of analytes absorbed by the polymeric coating can be expressed as:

$$n = \frac{K_0 V_f C_0 V_s}{K_0 V_f + V_s} \quad (1)$$

where n is the mass absorbed by the polymeric coating; $V_f$ and $V_s$ are the volumes of the fiber coating and the sample, respectively; $K_0$ is the partition coefficient of an analyte between the polymeric coating and sample matrix; $C_0$ is the initial concentration of the analyte in the sample. Since the polymeric coating is very small (about $10_{-3}$ mL) in most cases analytes in a matrix are not completely extracted. Since SPME is mainly an equilibrium extraction method, the concentration of an analyte in a matrix is determined by its linear relation with the amount of analyte extracted by the polymeric coating in accordance with equation (1) instead of the total extraction of the analyte. If the partition coefficient ($K_0$) is very large, then the term of $K_0 V_f$ is much larger than $V_s$ and equation (1) can be reduced to:

$$n = C_0 V_s \quad (2)$$

which means the analyte is totally extracted by the polymeric coating. Large hydrocarbon compounds such as PAH's often have very large partition coefficients and can be totally extracted by SPME. However, for most volatile organic compounds, values of $K_0$ are not large enough to meet the condition of $K_0 V_f$ being much larger than $V_s$ under normal circumstances.

In headspace SPME extraction, the volume of the headspace is usually 2 or 3 mL for a 2 gram sample (water or solid) and a 4 mL vial or container. The thickest coating for poly(dimethylsiloxane), which is the most frequently used coating for extraction of volatiles, is about 340 µm with 1 cm of length. This yields a volume $V_f = 2.4$ µL. For 90% extraction recovery (i.e. $n = 90\% \, C_0 V_s$), $K_0 V_f = 9 \, V_s$. This means that K0 must be larger than 7500. For BTEX compounds, the largest $K_0$ is 4400 for o-xylene, but for benzene, $K_0$ is only 493 at room temperature. Under these conditions, total extraction will not occur.

To achieve total extraction, a smaller sample volume $V_s$ could be used but this would require a smaller sample size which is not desirable for accurate analysis. Increasing the volume of the polymeric coating is another option but this is not practical since one of the most important advantages of SPME is its small dimension and the fact that no modification is required for the gas chromatograph injector. Another option, is to use a polymeric coating that has a strong affinity toward analytes and thus has very large $K_0$ values. The development of these coatings is not a simple matter and requires a great deal of time.

The same result can be achieved by increasing the $K_0$ values using a temperature gap between the polymeric coating and sample headspace. This approach not only increases K0 values but also facilitates the release of analytes from their matrix to the headspace and increases the efficiency and sensitivity of the extraction technique. By maintaining the polymeric coating at low temperature, additional advantages can be achieved.

The vial containing the sample is heated to an elevated temperature while simultaneously cooling the polymeric coating to prevent the coating from heating up. If the coating is not cooled as the sample is heated, the temperature of the coating would increase as the temperature of the sample increased and the temperature of the coating would be essentially the same as the temperature of the sample. The partition coefficient between the polymeric coating and headspace can increase very substantially due to the tendency of analytes to stay in the cooled polymeric coating.

In headspace SPME, there are three phases involved: sorbent, headspace and sample matrix. By assuming that the target analyte in a matrix can be completely released into the headspace during SPME, we can ignore the sample matrix. The transfer of the analyte from the gas phase to the sorbent will reduce the pressure since the volume of the container is kept constant during extraction. However, since the amount of analytes being absorbed is very small, the pressure change during extraction will be negligible.

Table I lists $K_T$ values of BTEX compounds at selected headspace temperatures. During the calculation, the average $C_p$ value of the compounds in the temperature range is used and the temperature unit should be in Kelvin. The coating is poly(dimethylsiloxane) and $T_f = 25°$ C. The partition coefficients of BTEX ($K_0$) at $T_s = T_f$ are also listed in Table I. Table I indicates that if the coating temperature is maintained at 25° C., as headspace temperature increases, the partition coefficient of the analyte increases dramatically. For example, toluene has a partition coefficient of 1322 when both the coating and headspace are at 25° C. Increasing headspace temperature to 227° C., while keeping the coating temperature at 25° C., causes the partition coefficient of toluene to increase to 31153. As mentioned before, to achieve total extraction of analytes, $K_T$ should have a value of 5000 or greater and preferably of 7500 or greater. The theoretical results indicate that for ethylbenzene and xylene isomers, $K_T$ will be larger than 7500 at approximately 100° C. while for benzene and toluene, $T_s$ will have to be much higher than 100° C.

TABLE I

The theoretical results of $K_T$ and other related parameters, $T_f = 25°$ C.

|  | $T_s(°C.)$ | $T_s(K)$ | $C_p(J.mol^{-1})$* | $C_p(ave)$# | $K_T/K_O$ | $K_T$ |
|---|---|---|---|---|---|---|
| Benzene | 27 | 300 | 83.02 | 82.73 | 1.006 | 496 |
| At 25° C. or | 77 | 350 |  | 90.36 | 1.360 | 670 |
| 298 K., | 127 | 400 | 113.52 | 97.98 | 2.355 | 1161 |
| $K_o = 493$ | 177 | 450 |  | 104.44 | 5.160 | 2539 |

TABLE I-continued

The theoretical results of $K_T$ and other related parameters, $T_f = 25°$ C.

| | $T_s$(°C.) | $T_s$(K) | $C_p$(J.mol$^{-1}$)* | $C_p$(ave)# | $K_T/K_O$ | $K_T$ |
|---|---|---|---|---|---|---|
| $C_p = 82.44$ J.mol$^{-1}$ | 227 | 500 | 139.35 | 110.90 | 14.184 | 6993 |
| Toluene | 27 | 300 | 104.42 | 104.08 | 1.006 | 1330 |
| At 25° C. or | 77 | 350 | | 112.96 | 1.412 | 1867 |
| 298 K., | 127 | 400 | 139.91 | 121.83 | 2.701 | 3571 |
| $K_o = 1322$ | 177 | 450 | | 129.54 | 6.917 | 9144 |
| $C_p = 103.75$ J.mol$^{-1}$ | 227 | 500 | 170.77 | 137.26 | 23.565 | 31153 |
| Ethylbenzene | 27 | 300 | 128.19 | 127.80 | 1.006 | 3286 |
| At 25° C. or | 77 | 350 | | 138.24 | 1.471 | 4804 |
| 298 K., | 127 | 400 | 169.95 | 148.68 | 3.152 | 10294 |
| $K_o = 3266$ | 177 | 450 | | 157.83 | 9.645 | 31500 |
| $C_p = 127.4$ J.mol$^{-1}$ | 227 | 500 | 206.68 | 166.99 | 41.769 | 136418 |
| m-Xylene | 27 | 300 | 126.46 | 126.08 | 1.006 | 3528 |
| At 25° C. or | 77 | 350 | | 136.04 | 1.466 | 5141 |
| 298 K., | 127 | 400 | 166.28 | 146.00 | 3.104 | 10886 |
| $K_o = 3507$ | 177 | 450 | | 154.87 | 9.315 | 32668 |
| $C_p = 125.71$ J.mol$^{-1}$ | 227 | 500 | 201.78 | 163.74 | 39.239 | 137611 |
| p-Xylene | 27 | 300 | 126.78 | 126.40 | 1.006 | 3528 |
| At 25° C. | 77 | 350 | | 136.57 | 1.467 | 5145 |
| 298 K., | 127 | 400 | 167.45 | 146.74 | 3.117 | 10931 |
| $K_o = 3507$ | 177 | 450 | | 155.70 | 9.406 | 32987 |
| $C_p = 126.02$ J.mol$^{-1}$ | 227 | 500 | 203.3 | 164.66 | 39.937 | 140059 |
| o-Xylene | 27 | 300 | 133.01 | 132.66 | 1.006 | 4444 |
| At 25° C. or | 77 | 350 | | 142.02 | 1.480 | 6537 |
| 298 K., | 127 | 400 | 170.46 | 151.38 | 3.201 | 14139 |
| $K_o = 4417$ | 177 | 460 | | 159.85 | 9.876 | 43622 |
| $C_p = 132.31$ J.mol$^{-1}$ | 227 | 500 | 204.32 | 168.32 | 42.848 | 189260 |

Benzene is difficult to quantitatively extract because of its small partition coefficient. However, by modifying the internally cooled SPME device to deliver a much larger flow of liquid $CO_2$, a lower polymer coating temperature $T_f$ will be achieved resulting in a larger temperature gap. The lower fiber coating temperature gives higher $K_0$ values for analytes because a liquid polymer absorbs organic compounds in what is usually an exothermic process, which results in more analytes being absorbed by the coating at lower temperature. A combination of larger $K_0$ and temperature gap gives a much larger temperature coefficient that will lead to the quantitative extraction of compounds normally having small partition coefficients such as benzene.

If the polymer is cooled to too low a temperature, the liquid coating may undergo glass transition and no longer be liquid. The diffusion process in such glass-like coating will be very low and adversely affect to coating performance. There may be another reason for low recovery of benzene. When sampling is completed, the flow of liquid $CO_2$ is turned off and the coating is no longer cooled. When the fiber coating was transferred into a gas chromatograph injector for thermal desorption and analysis, the temperature gap between the coating and its environment no longer existed. As a result, partition coefficients of analytes decreased and some analytes may have been lost. This problem can be solved through automation of the whole extraction process. The time period for the transfer a fiber coating into a GC injector can be shortened very significantly. The timing for turning off the flow of $CO_2$ may also be accurately controlled. If the temperature gap can be maintained until the fiber coating is within the injector, the loss of more volatile analytes can be avoided.

The internally cooled SPME device is not restricted to quantitative extraction. Any SPME extraction that involves heating can benefit from this device. For some very volatile compounds such as chloromethane, the quantitative extraction by SPME may not be possible even with a large temperature gap. But with the internally cooled SPME device, the sensitivity can be increased significantly compared with normal SPME extraction.

From Equation (1), it can be estimated that the partition coefficient must be over 5000 to achieve more than 90% recovery of analytes. Since the headspace temperature is 80° C., from Table I, it can be predicted that only xylene isomers in the recovery of BTEX compounds from aqueous and sand matrices will have recoveries over 90%. The actual results shown in Table II confirm this prediction. For Table II, methanol was used as a solvent during the preparation of the standard solution. During cooled SPME sampling, methanol as well as analytes were extracted by the coating. In order to eliminate the effect of solvent on the fiber coating, a BTEX/water batch solution was prepared by directly spiking BTEX pure compounds into water without using any solvent. Then, the BTEX/water solution was used to spike working samples such as sand. There was no organic solvent involved during the extraction. The results of the cooled SPME sampling of these samples is summarized in Table III. The quantitative extraction was achieved for all BTEX compounds except benzene. It can be concluded that the solvent involvement during sample preparation did not assist in extracting more analytes but actually hindered the extraction.

In Table IV, the same sample was extracted twice to determine whether the recovery could be calculated more accurately. From Table IV, it can be

TABLE II

The BTEX recovery for aqueous matrix.

| | aqueous matrix | | |
|---|---|---|---|
| | spiked (ng) | extracted (ng) | recovery |
| benzene | 2.0 | 1.0 | 50% |
| toluene | 2.0 | 1.3 | 66% |
| ethylbenzene | 2.0 | 1.7 | 85% |
| m,p-xylene | 2.0 | 1.8 | 90% |
| o-xylene | 2.0 | 2.0 | 100% |

TABLE III

The recovery of BTEX is sand matrix without solvent.

| | aqueous matrix | | |
|---|---|---|---|
| | spiked (ng) | extracted (ng) | recovery |
| benzene | 19.0 | 15.9 | 84% |
| toluene | 20.3 | 21.3 | 105% |
| ethylbenzene | 27.8 | 29.5 | 106% |
| m,p-xylene | 20.4 | 20.9 | 102% |
| o-Xylene | 25.5 | 25.5 | 100% |

TABLE IV

The recovery of BTEX is sand matrix determined by extracting the same sample twice

| | 1st extraction $n_1$(ng) | 2nd extraction $n_2$(ng) | recovery $(1-n_2/n_1)$ | recovery* |
|---|---|---|---|---|
| benzene | 15.9 | 3.2 | 80% | 84% |
| toluene | 21.3 | 1.8 | 91% | 105% |
| ethylbenzene | 29.5 | 1.6 | 95% | 106% |
| m,p-xylene | 20.9 | 0.7 | 97% | 102% |
| o-xylene | 25.5 | 1.0 | 96% | 100% |

*Recovery obtained by comparing with the spiked values (refer to Table VI).

seen that the method of sampling twice gives recovery values lower than 100% since there are also some trace analytes left in the matrix. Five of the six BTEX compounds achieved over 90% recovery when the same sample was extracted twice. Even benzene showed a recovery of 80%.

What I claim as my invention is:

1. A process for increasing analyte concentration in a sorbent from a source of analytes contained in a sample using a solid phase microextraction device with cooling means operatively connected to cool said sorbent, a sorbent and a sample containing a source of anayltes, said process comprising locating said sorbent where it can be contacted by said analytes of said sample, contacting said sorbent with said analytes, activating said cooling means, cooling said sorbent to increase the temperature differential between said sample and said sorbent, thereby increasing the analyte concentration in said sorbent.

2. A process as claimed in claim 1 including the step of increasing said temperature differential by heating said sample.

3. A process as claimed in claim 2 wherein said sample is located within a container having a headspace and said sorbent is located in said headspace, said process including the step of desorbing said analytes into said headspace whereby said analytes are absorbed from said headspace by said sorbent.

4. A process as claimed in claim 3 including the step of cooling said sorbent by contacting said sorbent with liquid carbon dioxide.

5. A process as claimed in claim 4 including the step of heating the sample by using one of a heat jacket, hot plate and microwave heating.

6. A process as claimed in claim 5 including the step of heating the sample until the headspace has a temperature of at least 80° C.

7. A process as claimed in claim 6 where the sorbent/sample has a partition coefficient, the sample has a volume and the sorbent has a volume, said process including the steps of increasing the temperature differential to a value where a sorbent/sample partition coefficient times a volume of the sorbent is at least ten times a volume of the sample.

8. A process as claimed in claim 7 wherein said method includes the steps of increasing a partition coefficient of said analytes between said sorbent and said sample to at least 5000 and the analytes are selected from the group consisting of compounds of benzene, toluene, ethylbenzene, xylene isomers, polyaromatic hydrocarbons, pesticides, aliphatics, phenols, ketones, acids, alcohols and organochlorine compounds.

9. A process as claimed in claim 1 including the steps of adding a reagent to said sample to cause an increased number of analytes to be release from said sample for absorption by said sorbent.

10. A process as claimed in claim 8 including the step of adding reagents to derivatize analytes in said sample into analogs having a higher affinity for said sorbent.

11. A process as claimed in claim 10 including the step of adding a reagent that is an acid until the pH is adjusted to approximately 1, the analytes entering the headspace being selected from the group consisting of phenols and acids.

12. A process as claimed in claim 11 including the step of adding salt to enhance extraction.

13. A process as claimed in claim 7 wherein the sorbent is a polymer and the anlytes contain carboxylic acids and chlorinated carboxylic acids, said process including the step of adding diazo reagents to said polymer to convert carboxylic acids and chlorinated carboxylic acids to esters.

14. A process as claimed in claim 13 wherein the diazo reagents are selected from the group consisting of 1-pyrenyldiazomethane and trimethylsilyl-diazomethane.

15. A process as claimed in claim 2 wherein the sorbent is a conductor, said process including the steps of concentrating the analytes by making the sorbent an electrode of an electrochemical cell and passing an electric current through said sorbent to deposit analytes thereon.

16. A process as claimed in claim 15 where said analytes contain acids and aldehydes including the step of using a polymer for said sorbent and reducing acids and aldehydes to less polar analogs.

17. A process as claimed in claim 13 including the step of using gold as said sorbent and gold-plated platinum as an electrode and reducing Hg2+ and (Hg)2+ to free mercury which is absorbed by said gold.

18. A process as claimed in claim 15 including the step of using mercury as said sorbent and mercury-coated carbon as the electrode and depositing metal ions.

19. A process as claimed in claim 2 including the step of agitating the sample selected from the group consisting of stirring, sonication and microwave heating.

20. A solid phase microextraction device for increasing analyte concentration in a sorbent from a source of analytes contained in a sample, said device consisting of a sorbent and a source of analytes contained in a sample, said sorbent being located to contact said sample, with cooling means operatively connected to cool said sorbent, and to thereby increase a temperature differential between said sample and said sorbent.

21. A device as claimed in claim 20 wherein the sample is located in a container.

22. A device as claimed in claim 21 wherein the sample has a head space and said sorbent is located in said head space.

23. A device as claimed in claim 22 wherein the cooling means is a Peltier cooling device.

24. A device as claimed in claim 22 wherein there are means to heat said sample simultaneously with the cooling of said sorbent.

25. A device as claimed in claim 24 wherein said sorbent is a coating to absorb said analytes, said coating being on a substrate.

26. A device as claimed in claim 25 wherein said sorbent has internal cooling means, said internal cooling means being located within said substrate.

27. A device as claimed in claim 26 wherein the internal cooling means is cooled using liquid carbon dioxide.

28. A device as claimed in claim 25 wherein said sorbent is selected from the group consisting of polymers and metallic sorbents.

29. A device as claimed in claim 25 wherein the coating is selected from the group consisting of polysiloxane, polyacrylate, carbowax, gold and an ion exchanger.

30. A device as claimed in any one of claims 20 or 21 wherein there are means to agitate the sample, said means being selected from the group consisting of stirring, sonication and microwave heating.

31. A device as claimed in claim 20 wherein there are means to transmit electromagnetic waves through said sorbent to detect and measure concentration of said analytes based upon absorbence of said waves by said sorbent containing said anayltes compared with absorbence of said waves by said sorbent when no analytes are present.

32. A device as claimed in claim 31 wherein the electromagnetic waves are light waves.

33. A device as claimed in claim 32 wherein the light waves are transmitted through the sorbent by fiber optics.

* * * * *